(12) United States Patent
Beckley

(10) Patent No.: US 12,282,029 B2
(45) Date of Patent: *Apr. 22, 2025

(54) PORTABLE DIAGNOSTIC SYSTEM FOR OVULATION CYCLE MONITORING

(71) Applicant: MFB Fertility, Inc., Erie, CO (US)

(72) Inventor: Amy Beckley, Erie, CO (US)

(73) Assignee: MPB Fertility, Inc., Erie, CO (US)

( * ) Notice: Subject to any disclaimer, the term of this patent is extended or adjusted under 35 U.S.C. 154(b) by 784 days.

This patent is subject to a terminal disclaimer.

(21) Appl. No.: 15/974,229

(22) Filed: May 8, 2018

(65) Prior Publication Data

US 2018/0321251 A1 Nov. 8, 2018

Related U.S. Application Data

(60) Provisional application No. 62/503,223, filed on May 8, 2017.

(51) Int. Cl.
*G01N 33/68* (2006.01)
*G01N 33/543* (2006.01)

(52) U.S. Cl.
CPC ..... *G01N 33/689* (2013.01); *G01N 33/54389* (2021.08)

(58) Field of Classification Search
CPC .... G01N 33/689; G01N 33/558; G01N 33/76; G01N 2333/59; G01N 35/00009; G01N 2035/00019; B01L 2300/0825
USPC ..... 422/401, 403, 404, 420, 425; 435/287.2, 435/287.7, 287.9, 288.7, 805, 810, 970, 435/973; 436/510, 514, 65, 169, 805, 436/810, 811, 814, 817, 818, 906
See application file for complete search history.

(56) References Cited

U.S. PATENT DOCUMENTS

| | | |
|---|---|---|
| 3,335,638 A | 8/1967 | John |
| 4,094,647 A | 6/1978 | Deutsch et al. |
| 4,168,146 A | 9/1979 | Grubb et al. |
| 4,235,601 A | 11/1980 | Deutsch et al. |
| 4,361,537 A | 11/1982 | Deutsch et al. |
| 4,376,110 A | 3/1983 | David et al. |

(Continued)

FOREIGN PATENT DOCUMENTS

| | | |
|---|---|---|
| CA | 3043270 A1 | 6/2018 |
| CN | 106146651 A | 11/2016 |

(Continued)

OTHER PUBLICATIONS

Goel et al. ("Plasticity within the Antigen Combining Site May Manifest as Molecular Mimicry in the Humoral Immune Response," The Journal of Immunology (2004), 173(12):7358-7367) (Year: 2004).*

(Continued)

*Primary Examiner* — Christopher L Chin
(74) *Attorney, Agent, or Firm* — MORRISON & FOERSTER LLP

(57) ABSTRACT

The preferred embodiment of the resent invention is described as an in-home diagnostic system used to monitor ovulation cycles. In embodiments, the invention allows for users to evaluate early pregnancy status without medical training. Embodiments of the invention comprise a method incorporating usage of a smart device to allow for analysis of multiple analytes present within a single sample placed upon a lateral flow assay test cassette.

7 Claims, 2 Drawing Sheets

(56) References Cited

U.S. PATENT DOCUMENTS

| | | |
|---|---|---|
| 4,450,239 A | 5/1984 | Chatterton |
| 4,703,017 A | 10/1987 | Campbell et al. |
| 4,775,636 A | 10/1988 | Moeremans et al. |
| 4,855,240 A | 8/1989 | Rosenstein et al. |
| 4,857,453 A | 8/1989 | Ullman et al. |
| 4,861,711 A | 8/1989 | Friesen et al. |
| 4,943,522 A | 7/1990 | Eisinger et al. |
| 4,952,517 A | 8/1990 | Bahar |
| 5,158,869 A | 10/1992 | Pouletty et al. |
| 5,252,496 A | 10/1993 | Kang et al. |
| 5,384,264 A | 1/1995 | Chen et al. |
| 5,424,193 A | 6/1995 | Pronovost et al. |
| 5,602,040 A | 2/1997 | May et al. |
| 6,156,271 A | 12/2000 | May |
| 6,319,676 B1 | 11/2001 | Nazareth et al. |
| 6,352,862 B1 | 3/2002 | Davis et al. |
| 6,451,619 B1 | 9/2002 | Catt et al. |
| 6,699,722 B2 | 3/2004 | Bauer et al. |
| 6,924,153 B1 | 8/2005 | Boehringer et al. |
| 7,044,919 B1 | 5/2006 | Catt et al. |
| 7,144,742 B2 | 12/2006 | Boehringer et al. |
| 7,483,054 B2 | 1/2009 | Lin et al. |
| 7,943,395 B2 | 5/2011 | Wei et al. |
| 9,063,091 B2 | 6/2015 | Tsai et al. |
| 9,206,254 B2 | 12/2015 | Decourtye et al. |
| 9,386,221 B2 | 7/2016 | Kauniskangas et al. |
| 9,787,815 B2 | 10/2017 | Erickson et al. |
| 9,857,373 B1 | 1/2018 | Pulitzer et al. |
| 9,939,385 B2 | 4/2018 | Nazareth et al. |
| 11,029,321 B2 | 6/2021 | Beckley |
| 11,061,026 B2 | 7/2021 | Beckley |
| 11,131,665 B1 | 9/2021 | Beckley |
| 11,573,225 B2 | 2/2023 | Beckley |
| 11,855,659 B2 | 12/2023 | Nishikawa et al. |
| 2004/0253142 A1 | 12/2004 | Brewster et al. |
| 2005/0130311 A1 | 6/2005 | Coley et al. |
| 2005/0171454 A1 | 8/2005 | Catt et al. |
| 2005/0196875 A1 | 9/2005 | Blatt et al. |
| 2006/0008896 A1 | 1/2006 | Nazareth et al. |
| 2006/0121626 A1 | 6/2006 | Imrich |
| 2009/0137478 A1 | 5/2009 | Bernstein et al. |
| 2009/0228303 A1 | 9/2009 | Faulkner et al. |
| 2010/0312137 A1 | 12/2010 | Gilmour et al. |
| 2012/0038820 A1 | 2/2012 | Kempahonnaiah |
| 2012/0040386 A1 | 2/2012 | Knappe et al. |
| 2012/0119984 A1 | 5/2012 | Sankarasubramaniam et al. |
| 2012/0197539 A1 | 8/2012 | Slupsky |
| 2012/0321519 A1 | 12/2012 | Brown |
| 2013/0034908 A1 | 2/2013 | Barstis et al. |
| 2013/0065321 A1 | 3/2013 | Nazareth et al. |
| 2013/0273563 A1 | 10/2013 | Ehrenkranz |
| 2014/0051173 A1 | 2/2014 | Barstis et al. |
| 2014/0147838 A1 | 5/2014 | Sempere et al. |
| 2014/0320677 A1 | 10/2014 | Jarvenpaa et al. |
| 2015/0032008 A1 | 1/2015 | Landesman |
| 2015/0057551 A1 | 2/2015 | Chou et al. |
| 2015/0094227 A1* | 4/2015 | McCarthy ............ G01N 33/743 506/9 |
| 2015/0109323 A1 | 4/2015 | Johnson et al. |
| 2015/0304555 A1 | 10/2015 | Ehrenkranz |
| 2015/0338387 A1 | 11/2015 | Ehrenkranz |
| 2016/0139156 A1 | 5/2016 | Lakdawala |
| 2016/0167042 A1 | 6/2016 | Tyrrell et al. |
| 2016/0178629 A1 | 6/2016 | Husheer et al. |
| 2016/0188937 A1 | 6/2016 | Tyrrell et al. |
| 2016/0194718 A1 | 7/2016 | Lane et al. |
| 2016/0210427 A1 | 7/2016 | Mynhier et al. |
| 2016/0370389 A1 | 12/2016 | Barstis et al. |
| 2017/0007215 A1 | 1/2017 | Podoly |
| 2017/0011194 A1 | 1/2017 | Arshad et al. |
| 2017/0327023 A1 | 11/2017 | Leurck et al. |
| 2018/0088136 A1 | 3/2018 | Saji et al. |
| 2018/0106799 A1 | 4/2018 | Brenner et al. |
| 2018/0129722 A1 | 5/2018 | Bormann et al. |
| 2018/0196037 A1 | 7/2018 | Polwart et al. |
| 2018/0366232 A1 | 12/2018 | Dvorak et al. |
| 2019/0027251 A1 | 1/2019 | Pulitzer et al. |
| 2019/0073763 A1 | 3/2019 | Li et al. |
| 2019/0212353 A1 | 7/2019 | Yang et al. |
| 2019/0310576 A1 | 10/2019 | Tomii et al. |
| 2019/0341127 A1 | 11/2019 | Lo et al. |
| 2020/0078781 A1 | 3/2020 | Beckley |
| 2020/0141953 A1 | 5/2020 | Beckley |
| 2020/0141954 A1 | 5/2020 | Beckley |
| 2020/0152038 A1 | 5/2020 | Herbst et al. |
| 2021/0055310 A1 | 2/2021 | Beckley |
| 2021/0231574 A1 | 7/2021 | Wang et al. |
| 2021/0293800 A1 | 9/2021 | Beckley |
| 2021/0293809 A1 | 9/2021 | Beckley |
| 2021/0389311 A1 | 12/2021 | Beckley |
| 2022/0146408 A1 | 5/2022 | Koudele et al. |
| 2022/0341951 A1 | 10/2022 | Beckley et al. |
| 2023/0064561 A1 | 3/2023 | Beckley |
| 2023/0068803 A1 | 3/2023 | Heikenfeld et al. |
| 2023/0248814 A1 | 8/2023 | Wu et al. |
| 2023/0374143 A1 | 11/2023 | Kjølby et al. |
| 2023/0408512 A1 | 12/2023 | Beckley |
| 2024/0058805 A1 | 2/2024 | Beckley |

FOREIGN PATENT DOCUMENTS

| | | |
|---|---|---|
| CN | 104697938 B | 4/2018 |
| EP | 158746 A2 | 10/1985 |
| EP | 276152 A2 | 7/1988 |
| EP | 306772 A1 | 3/1989 |
| EP | 451800 A1 | 10/1991 |
| EP | 656118 B1 | 2/1997 |
| EP | 1066530 B1 | 11/2004 |
| EP | 2788764 A1 | 10/2014 |
| EP | 2839264 A1 | 2/2015 |
| EP | 2861991 A1 | 4/2015 |
| EP | 3052944 A1 | 8/2016 |
| GB | 2204398 B | 8/1991 |
| WO | WO-1994004924 A1 | 3/1994 |
| WO | WO-1995016920 A1 | 6/1995 |
| WO | WO-1998039657 A1 | 9/1998 |
| WO | WO-2006010072 A2 | 1/2006 |
| WO | WO-2007049157 A2 | 5/2007 |
| WO | WO-2013188860 A1 | 12/2013 |
| WO | WO-2015049510 A1 | 4/2015 |
| WO | WO-2015116854 A1 | 8/2015 |
| WO | 2016115608 A1 | 7/2016 |
| WO | WO-2016142610 A1 | 9/2016 |
| WO | 2016166415 A1 | 10/2016 |
| WO | 2017058827 A1 | 4/2017 |
| WO | 2017180909 A1 | 10/2017 |
| WO | WO-2017198204 A1 | 11/2017 |
| WO | WO-2018236792 A1 | 12/2018 |
| WO | WO-2019023926 A1 | 2/2019 |
| WO | WO-2019133920 A1 | 7/2019 |
| WO | WO-2019246361 A1 | 12/2019 |
| WO | WO-2021034412 A1 | 2/2021 |
| WO | WO-2023069366 A1 | 10/2022 |

OTHER PUBLICATIONS

Lloyd et al. ("Modelling the human immune response: performance of a 1011 human antibody repertoire against a broad panel of therapeutically relevant antigens," Protein Engineering, Design & Selection (2009), 22(3):159-168) (Year: 2009).*

Edwards et al. ("The remarkable flexibility of the human antibody repertoire; isolation of over one thousand different antibodies to a single protein, BlyS," Journal of Molecular Biology (2003), 334:103-118) (Year: 2003).*

Lewis et al., (1990). "Monoclonal antibodies to pregnanediol-3-glucuronide: application to a direct enzyme-linked immunosorbent assay of urine," Science Direct, Steroids, 55(7):314-318. Abstract only.

Lewis et al., (2009). "ZZ polyester beads: An efficient and simple method for purifying IgG from mouse hybridoma supernatants," Journal of Immunological Methods, 346:71-74.

(56) References Cited

OTHER PUBLICATIONS

Unpublished U.S. Appl. No. 18/094,261, filed Jan. 6, 2023 titled "System for Evaluating Urine for the Presence or Absence of Pregnanediol Glucuronide and Other Hormones and Analytes," (Copy not submitted herewith pursuant to the waiver of 37 C.F.R. § 1.98(a)(2)(iii)).
Unpublished U.S. Appl. No. 18/106,834, filed Feb. 7, 2023 titled "Wearable Device for Continuous Monitoring of Target Hormones And/Or Other Analytes, and Methods of Using Thereof," (Copy not submitted herewith pursuant to the waiver of 37 C.F.R. § 1.98(a)(2)(iii)).
Unpublished U.S. Appl. No. 18/125,590, filed Mar. 23, 2023 titled "Systems and Methods for Tracking Progesterone," (Copy not submitted herewith pursuant to the waiver of 37 C.F.R. § 1.98(a)(2)(iii)).
Unpublished U.S. Appl. No. 17/897, 132, filed Aug. 27, 2020 titled "Systems and Methods of Detecting Hormones or Analytes for Fertility and Pregnancy Monitoring," (Copy not submitted herewith pursuant to the waiver of 37 C.F.R. § 1.98(a)(2)(iii)).
Unpublished U.S. Appl. No. 17/822,773, filed Aug. 27, 2020 titled "Ovulation Monitoring Platform," (Copy not submitted herewith pursuant to the waiver of 37 C.F.R. § 1.98(a)(2)(iii)).
Unpublished U.S. Appl. No. 29/788,306, filed Apr. 29, 2021 titled "Female Health Application User Interface," (Copy not submitted herewith pursuant to the waiver of 37 C.F.R. § 1.98(a)(2)(iii)).
Partial European Search Report and Written Opinion received for European Patent Application No. 20854747.1 mailed on Aug. 3, 2023, 23 pages.
Bouchard et al., (2019). "Pilot Evaluation of a New Urine Progesterone Test to Confirm Ovulation in Women Using a Fertility Monitor," Front. Public Health, 7:184, 4 pages.
Ecochard et al., (2013). "Use of urinary pregnanediol 3-glucuronide to confirm ovulation," Steroids, 78:1035-1040.
Extended European Search Report and Written Opinion received for European Patent Application No. 18895132.1 mailed on Sep. 9, 2021, 12 pages.
Googleplay, (2015). "DaysyView" Valley Electronics, 5 pages.
Hermanson, (1996). "Chapter 20: Antibody Modification and Conjugation," Bioconjugate Techniques, pp. 783-823.
Indiegogo, (2017). "At Home Ovulation Double Check Test," available online at <https://www.indiegogo.com/projects/at-home-ovulation-double-check-test#/>, 14 pages.
International Search Rport and Written Opinion for International Patent Application No. PCT/US2021/72306 mailed on Feb. 3, 2022, 10 pages.
Kerrigan et al., (2001). "Comparison of ELISAs for Opiates, Methamphetamine, Cocaine Metabolite, Benzodiazepines, Phencyclidine, and Cannabinoids in Whole Blood and Urine," Clinical Chemistry, 47(3):540-547.
Koczula et al., (2016). "Lateral flow assays," Essays in Biochemistry, 60:111-120.
Leiva et al., (2019). "Pilot observational prospective cohort study on the use of a novel home-based urinary pregnanediol 3-glucuronide (PDG) test to confirm ovulation when used as adjunct to fertility awareness methods (FAMs) stage 1," BMJ Open, 9:e028496, 8 pages.
Maggio, (1980). "Chapter 3: Enzymes as Immunochemical Labels," Enzyme Immunoassay CRC Press, 54-70. Abstract Only.
Merriam-Webster, (2020). "Definition: base unit," Available online at <https://www.merriam-webster.com/dictionary/base unit>, 10 pages.
Mesen et al., (2015). "Progesterone and the Luteal Phase: A Requisite to Reproduction," Obstetrics and Gynecology Clinics of North America, 42(1):135-151, 19 pages.
Munro et al., (1991). "Relationship of Serum Estradiol and Progesterone Concentrations to the Excretion Profiles of Their Major Urinary Metabolites as Measured by Enzyme Immunoassay and Radioimmunoassay," Clinical Chemistry, 37(6):838-844.
Pauillac et al., (1998). "An improved method for the production of antibodies to lipophilic carboxylic hapten using small amount of hapten-carrier conjugate," Journal of Immunological Methods, 220:105-114. Abstract Only.
PCT International Search Report with attached Written Opinion of the International Searching Authority for International Application No. PCT/US2018/68027, dated Mar. 26, 2019, 16 pages.
PCT International Search Report with attached Written Opinion of the International Searching Authority for International Application No. PCT/US2020/40600, dated Nov. 20, 2020, 13 pages.
Santoro et al., (2012). "Reproductive Hormones and the Menopause Transition," Obstet Gynecol Clin North Am., Author manuscript available online at <https://www.ncbi.nlm.nih.gov/pmc/articles/PMC3197715/>, 15 pages.
Su et al., (2013). "Hormone changes associated with the menopausal transition," Minerva Ginecol., Author manuscript available online at <https://www.ncbi.nlm.nih.gov/pmc/articles/PMC3823936/>, 9 pages.
Su et al., (2017). "Detection of ovulation, a review of currently available methods," Bioeng Transl Med., 16:238-246.
Vyjayanthi et al., (1995). "Binding characteristics of bovine serum albumin-afloxin B1 to polystyrene microtiter plates: Importance of hapten to carrier protein molar ratio," Indian Journal of Experimental Biology, 33:329-332. Abstract Only.
Youtube, (2017). "How do Ovulation Double Check Tests work," Available online at <https://www.youtube.com/watch?v=HX-yNp>, 1 page.
Youtube, (2018). "Testing progesterone at home: MFB Proov test," Available online at <https://m.youtube.com/watch?v=zjMR9FDQip0>, 1 page.
MFB Fertility, Inc. (2017). "Ovulation Double Check, Catalog # MFB-01," retrieved online from <https://nebula.wsimg.com/9d9ad3495de83e7be3d53247867b8966?AccessKeyId=DA50EDF93F4AF80A8854&disposition=0&alloworigin=1>, 2 pages.
Unpublished U.S. Appl. No. 17/522,696, filed Nov. 9, 2021 titled "Method for Detection and Interpretation of Results Indicated On a Photographed Diagnostic Test," (Copy not submitted herewith pursuant to the waiver of 37 C.F.R. § 1.98(a)(2)(iii)).
Unpublished U.S. Appl. No. 17/636,755, filed Jul. 2, 2020 titled "Systems and Methods for Menstrual Cycle Testing," (Copy not submitted herewith pursuant to the waiver of 37 C.F.R. § 1.98(a)(2)(iii)).
Liu et al., (2012). "Case Studies of Minimizing Nonspecific Inhibitors in HTS Campaigns That Use Assay-Ready Plates," Journal of Biomolecular Screening, 17(2):225-236.
Unpublished U.S. Appl. No. 18/696,892, filed Mar. 8, 2024 titled "Devices, Systems and Methods for Detection of Beta Subunit of Luteinizing Hormone," (Copy not submitted herewith pursuant to the waiver of 37 C.F.R. § 1.98(a)(2)(iii)).

* cited by examiner

PORTABLE DIAGNOSTIC SYSTEM FOR OVULATION CYCLE MONITORING

CROSS-REFERENCE TO RELATED APPLICATIONS

This application claims the benefit of U.S. Provisional Patent Application 62/503,223, filed on May 8, 2017, which is incorporated by reference herein in its entirety.

BACKGROUND OF THE INVENTION

The present inventor has recognized the problem of remote hormone monitoring. Currently, quantitative reproductive hormone monitoring cannot be performed remotely. Remote hormone monitoring is important to increase access to care for infertility diagnosis and treatment. Currently only 25% of women that need infertility treatment have access to care.

In association with prior art solutions, to test hormone levels, many women had to travel to a limited number of clinical labs able to perform quantitative reproductive hormone analysis. In many locations, women were required to drive several hours to the nearest clinic. Similar prior art solutions involving monthly hormone monitoring are expensive, time consuming, and often require missed work.

Alternatively, in association with prior art solutions, women would be required to collect blood samples and mail them to a lab for processing. However, such a process takes 3-7 days. Yet effective infertility treatment and diagnosis often needs same day results. Thus, prior art solutions for infertility treatment and diagnosis are often too slow and therefore ineffective.

Diagnostic tests for screening analytes, e.g. urinary hormones or metabolites thereof, may utilize antibodies specific to the analyte. A change in the level from a predetermined threshold level may be noted by differences in color or color intensity compared with the color in a reference window or reference guide. The color change may be produced using techniques such as enzyme-linked immunosorbent assays or lateral flow color matching assays to indicate the amount of analyte in a urine sample.

SUMMARY OF THE INVENTION

Figure 1:
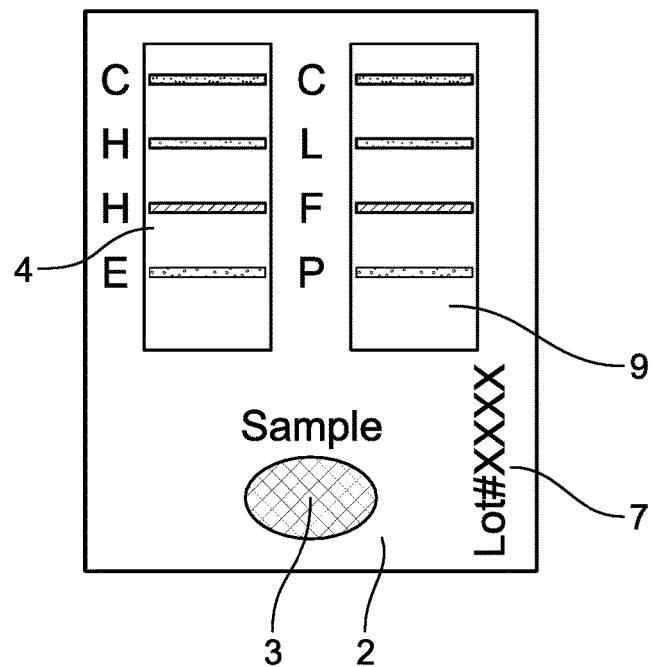
FIG. 1 depicts disposable lateral flow assay test cassette in an embodiment of the invention.

The preferred embodiment of the present invention is described as an in-home diagnostic system used to monitor ovulation cycles. In embodiments, the invention allows for users to evaluate early pregnancy status without medical training. Embodiments of the invention comprise a method incorporating usage of a smart device to allow for analysis of multiple analytes present within a single sample placed upon a lateral flow assay test cassette.

DETAILED DESCRIPTION

In varying embodiments, the invention may incorporate any subset of, or all of, the following components: (1.) test cassette reader, (2.) disposable lateral flow assay tests cassette, (3.) sample well, (4.) detection zone, (5.) wicking material, (6.) plastic housing, (7.) unique identifier, (8.) labelled secondary reagent, (9.) test strip.

Generally, aspects of embodiments of the present invention relate to unique and novel adaptations and/or configurations of quantitative lateral flow assays and devices, such as those described in U.S. Pat. No. 6,924,153, which is incorporated by reference in its entirety herein. Generally, aspects of embodiments of the present invention relate to unique and novel adaptations and/or configurations associated with positive detection lateral-flow apparatus and methods for small and large analytes, such as those described in U.S. Pat. No. 6,699,722, which is incorporated by reference in its entirety herein. Generally, aspects of embodiments of the present invention relate to unique and novel adaptations and/or configurations associated with systems, methods and test kits for analyte variation detection, such as those described in U.S. Pat. No. 9,939,385, which is incorporated by reference in its entirety herein. Generally, aspects of embodiments of the present invention relate to unique and novel adaptations and/or configurations of ovulation cycle monitoring and management, such as those described in U.S. patent application Ser. No. 12/084,166, filed on Oct. 24, 2006, which is incorporated by reference in its entirety herein. Generally, aspects of embodiments of the present invention relate to, and/or are used in association with, unique and novel adaptations and/or configurations of pregnancy test devices and methods, such as those described in U.S. patent application Ser. No. 14/505,083, filed on Oct. 2, 2014, which is incorporated by reference in its entirety herein. Generally, the devices and methods of embodiments of the present invention employ lateral flow assay techniques and matrices capable of bibulous and/or nonbibulous lateral flow as generally described in U.S. Pat. Nos. 5,424,193, 4,943,522; 4,861,711; 4,857,453; 4,855,240; 4,775,636; 4,703,017; 4,361,537; 4,235,601; 4,168,146; 4,094,647; U.S. patent application Ser. No. 07/639,967, European Patent Application Nos. 451,800; 158,746; 276,152; 306,772 and British Patent Application No. 2,204,398; each of which is incorporated in its entirety herein by reference. Aspects of the invention relate to a test strip known in the art and improvements thereon, such as a test strip as described in U.S. Pat. No. 6,319,676, the entire content of which is hereby incorporated by reference.

An embodiment of the invention incorporates a test cassette reader 1. A test cassette reader 1 in an embodiment of the invention is described as an image capture device to allow for the visual capture of the color intensity in each detection zone. A test cassette reader 1 in an embodiment of the invention is also described as a smart phone and or tablet application utilizing the camera of the smart phone or tablet to capture the results displayed in a lateral flow assay test cassette via photography, and then analyze and interpret the results displayed. In an embodiment, the test cassette reader 1 may further comprise a clip or other positioning device to optimize the positioning of the disposable lateral flow assay tests cassette 2 in relation to a smart phone, tablet or similar device as known by those skilled in the art, to facilitate lateral flow cassette imaging, in association with a smart phone or tablet application.

The preferred embodiment of the invention incorporates a disposable lateral flow assay tests cassette 2. The disposable lateral flow assay tests cassette 2 in an embodiment of the invention is described as a device intended to facilitate the collection of a sample. In the preferred embodiment, the sample comprises either serum, whole blood or urine. In an embodiment, the disposable lateral flow assay tests cassette 2 incorporates one or more test strips 9. In an embodiment of an invention, the one or more test strips 9 comprise a diagnostic reagent strip as one skilled in the art recognizes is utilized in association with common testing technologies in routine clinical use. In an embodiment of the invention, the one or more test strips 9 are configured to evaluate one or more analytes.

In an embodiment, the disposable lateral flow assay tests cassette 2 is configured to allow the sample to permeate through the one or more test strips into or through one or more detection zones, each optionally comprising a reagent-impregnated membrane, contained within each test strip 9. In varying embodiments, the device further comprises a sample well, wicking material, a plastic housing and a unique identifier.

The device is further configured such that one or more analytes present in the sample can therefore become bound within the one or more detection zones. The device is further configured such that the extent to which one or more analytes become bound are determinable by labeled secondary reagents. In an embodiment, the color intensity in the one or more detection zones is directly correlated with the concentration of the analyte in the sample.

In an embodiment, the disposable lateral flow assay test cassette utilizes a sample, optionally comprising a single blood, serum, saliva, or urine sample, to analyze five different analytes and an internal assay control. An embodiment of the invention incorporates a sample well 3 designed to collect and receive a sample, configured to facilitate transfer of the sample to one or more test strips. An embodiment of the invention further incorporates a plastic housing 6. In an embodiment, the sample well 3 is an aperture contained within the plastic housing 6.

An embodiment of the invention incorporates a detection zone 4. A detection zone 4 in an embodiment of the invention is described as a reagent-impregnated membrane located within one or more test strips. A detection zone 4 in an embodiment of the invention is also described as an area of the one or more test strips coated with specific binding partner, configured to enable analytes present in the sample to therefore become bound. In an embodiment of the invention, the sample applied is a single sample, and the device is configured to detect the presence of multiple discrete analytes present in the sample.

In association with embodiments of the invention, release and capture media are joined together to form a single liquid path in association with a lateral flow assay. Reagents for detecting labeling and capturing the analyte (or hormone) of interest are disposed on a release and capture media. Located on the release medium is a binding member reactive with a first epitope of the analyte of interest, for example LH, FSH, P4, hCG and pregnanediol. The binding member is labeled with a detectable marker. A capturable component is located on the release medium downstream of the binding member, which component comprises a binding agent reactive with a second epitope of the analyte and one member of an affinity pair. The capturable component is capable of forming a complex with the labeled binding member and the analyte. The labeled binding member and the capturable component both are releasably bound to the release medium such that when the solvent front created by the liquid sample being analyzed passes through the release medium, the labeled binding member and the capturable component both become solubilized by the liquid and flow with the solvent along the liquid path. In operation, if any analyte is present in the liquid sample, it reacts first with the labeled binding member, then with the capturable component as the front advances along the liquid path. By the time the solvent front reaches the capture medium section of the biphasic material, also referred to herein as a detection zone, the capturable complex has formed. The capture site located on the capture medium comprises the other member of the affinity pair specific for the capturable component. The affinity member is immobilized, preferably by simple adsorption, at the capture site, and does not advance with the solvent front. In a preferred embodiment, a control site also is located on the capture medium downstream of the capture site. The control site has immobilized thereon a binding agent having an affinity for the labeled binding member. The binding agent will capture any labeled binding member which is not captured at the upstream capture site. In operation, the presence of the detectable marker at the control site indicates that sorptive transport has operated properly.

In operation, if any analyte is present in the liquid sample, it reacts first with the labeled binding member, then with the capturable component as the front advances along the liquid path. By the time the solvent front reaches the capture medium section of the biphasic material, the capturable complex has formed. Polyclonal antisera and monoclonal antibodies or fractions thereof having specific binding properties and high affinity for virtually any antigenic substance which are useful in the present invention as binding members and capture materials are known and commercially available, or can be produced from stable cell lines using well known cell fusion and screening techniques. The literature is replete with protocols for producing and immobilizing proteins. See, for example, Laboratory Techniques in Biochemistry and Molecular Biology, Tijssen, Vol. 15, Practice and Theory of Enzyme immunoassays, chapter 13, The Immobilization of Immunoreactants on Solid Phases, pp. 297-328, and the references cited therein. The method of the invention also may be designed to exploit conventional "sandwich" or "competitive" techniques. In the case of the sandwich technique, the labeled binding member comprises an antibody which binds to an epitope on the analyte of interest to form a labeled antibody-antigen complex. This complex then migrates to the capture site to react with a capturable component which, in this embodiment, comprises a second antibody specific for a second epitope of said analyte. For example, in the case of biotin, the affinity member may be streptavidin. At the capture site, the analyte and labeled antibody reacts with the immobilized capture member to form a "sandwich" of the second antibody, analyte and labeled antibody. This sandwich complex is progressively produced at the capture site as sample continuously passes by. As more and more labeled conjugate is immobilized at the capture site, the colored particles aggregate and become visible through the window of the casing, indicating the presence of the analyte in the liquid sample. Both in the presence or absence of a detectable level of analyte, the colored particles gather at the control site which also is visible through the window. In the case of the competitive technique, a known amount of the analyte (or hormone) of interest is present on the release medium disposed upstream of an antibody specific for it. The analyte present in the release medium is labeled. The labeled analyte on the release medium may comprise, for example, an authentic sample of the analyte, or a fraction thereof which has comparable affinity for the antibody. As the liquid sample is transported along the release medium, the labeled analyte present on the release medium and any unlabeled analyte present in the sample compete for sites of attachment to the antibody. If no analyte is present in the sample, labeled analyte-antibody aggregates at the capture site, and the presence of color indicates the absence of detectable levels of analyte in the sample. If analyte is present, the amount of labeled analyte which binds at the test site is reduced because of binding of analyte in the sample with the antibody, and no color, or a paler color, develops.

In an embodiment, the immunoassay device of the present invention is designed to detect human pregnancy. In this embodiment, the labeled binding member is a monoclonal antibody (MAb) against human chorionic gonadotropin (hCG) labeled with colloidal gold. For this purpose, MAb designated 2G9 (available from Carter-Wallace, Inc.) is preferred. Anti-hCG antibodies labeled with biotin are used for the capturable complex in an embodiment. Monoclonal antibodies which can be used for this purpose include the hCG specific monoclonal antibodies designated 2B2 and B109 (available from Carter-Wallace, Inc.) and CCF01 (available from Scripps Laboratory). Methods for conjugating biotin to antibodies are well-known and do not form a part of the present invention. In the present preferred embodiment, the capture site comprises streptavidin, which has a high affinity for biotin. A control site preferably is located downstream of the capture site. The control site has immobilized thereon goat anti-mouse IgG specific for the labeled anti-hCG (available from Scantibodies Laboratory).

In another preferred embodiment the present immunoassay device is designed to detect human ovulation. In this embodiment, the labeled binding member comprises MAb 2G9, which is specific for luteinizing hormone (LH) and hCG, labeled with colloidal gold. The capturable complex comprises biotinylated LH-specific MAb LH26 (available from Carter-Wallace, Inc.). The capture site preferably comprises streptavidin and the control site comprises goat anti-mouse IgG specific for the labeled MAb. Further, in various embodiments the device may similarly assay other analytes such as, FSH and progesterone, estrogen or metabolites thereof.

In an embodiment, the disposable lateral flow assay tests cassette 2 is configured to simultaneously measure and/or indicate two or more of the following: (1), Estradiol (E2) at concentrations 25-250 pg/ml in a competitive assay format; (2), Follicle Stimulating Hormone (FSH) at concentrations 3-20 mIU/ml in a sandwich assay format; (3), Luteinizing Hormone (LH) at concentrations 0-25 mIU/ml in a sandwich assay format; (4), Progesterone (P4) at concentrations of 0-40 ng/ml in a competitive or sandwich assay format; (5) human chorionic gonadotropin, (hCG) at concentrations of 0-10,000 mIU/ml; in a sandwich assay format, and (6) an internal assay control.

In an alternative embodiment, the disposable lateral flow assay tests cassette 2 is configured to simultaneously measure the following hormones in urine: progesterone metabolites, including pregnanediol, within the range of 0-20 micrograms/milliliter; estrogen metabolites, including estrone, within the range of 0-1000 nanograms/milliliter. In associated with methods known by those skilled in the art, the configuration of the lateral flow assay tests cassette 2 is accomplished by altering the concentration and composition of substrates impregnated on the membrane and/or by altering the sensitivity of the conjugated antibody.

As referred to herein, in an embodiment, the "reagent-impregnated membrane" described in the preceding paragraphs comprises, and the antibody associated with the "conjugated antibody" relevant to the detection of PdG referred to in the preceding paragraph consists of a monoclonal anti-PdG antibody, and more specifically the monoclonal anti-PdG antibody having the necessary binding affinity for PdG such that when used in association with the invention as described herein it is capable of yielding a detection threshold of PdG of 1-20 μg/mL, which has been deposited in accordance with the provisions of the Budapest Treaty at the American Type Culture Collection (ATCC), located at the following address: 10801 University Boulevard, Manassas, VA 20110 USA on Apr. 23, 2021. The accession number of the deposit is Patent Deposit Number PTA-127054. The deposited material is a biological material specifically identified in the application, namely the conjugated antibody consisting of a monoclonal anti-PdG antibody as specifically referred to herein.

In the preferred embodiment, estrogen and progesterone are measured using a competitive assay while LH, FSH and hCG are measured using a sandwich assay. In an alternative embodiment, estrogen and progesterone are measured using a sandwich assay.

The present inventors have recognized the benefit of a configuration of the preferred embodiment of the invention to simultaneously analyse five (5) analytes. Those five (5) analytes that the disposable lateral flow assay test cassette will simultaneously measure in the preferred embodiment, and the methods of measurement, are:

1. Estradiol (E2) at concentrations 25-3,000 pg/ml in a competitive assay format. In association with the preferred method of use, immobilized E2 will be impregnated onto the membrane and anti-E2 antibodies will be labeled and migrate to the detection zone upon sample application. In an embodiment, when utilized in association with urine, a measurement may detect any urine metabolites of estradiol, in particular any metabolites in the following ranges of concentrations: 0-1000 ng/ml.
2. Follicle Stimulating Hormone (FSH) at concentrations 0-30 mIU/ml in a sandwich assay format. In association with the preferred method of use, an impregnating step facilitates impregnation of immobilized anti FSH onto the membrane, a labeling step facilitates anti-FSH antibodies to be labeled, and a migrating step facilitates anti-FSH antibodies to migrate to the detection zone upon sample application.
3. Luteinizing Hormone (LH) at concentrations 0-50 mIU/ml in a sandwich assay format. In association with the preferred method of use, an impregnating step facilitates impregnation of immobilized anti LH onto the membrane, a labeling step facilitates the labeling of anti-LH antibodies, and a migrating step facilitates anti-LH antibodies to migrate to the detection zone upon sample application.
4. Progesterone (P4) 0-60 ng/ml in a competitive assay format. In association with the preferred method of use, an impregnating step facilitates impregnation of immobilized P4 to be impregnated onto the membrane, a labeling step facilitates the labeling of anti-P4 antibodies, and a migrating step facilitates migration to the detection zone upon sample application. In an embodiment, when utilized in association with urine, a measurement may detect any urine metabolites of progesterone, in particular any urine metabolites in the following ranges of concentrations: 0-20 mcg/ml.
5. hCG at concentrations of 0-10,000 mIU/ml in a sandwich assay format. In association with the preferred method of use, an impregnating step facilitates impregnation of immobilized anti-hCG antibodies onto the membrane, a labelling step facilitates labeling of and anti-hCG antibodies, and a migrating step facilitates migration to the detection zone upon sample application.

6. Internal assay control is a sandwich assay format where immobilized anti-IgG antibodies will be impregnated onto the membrane during an impregnating step, and all labeled antibodies can migrate to the control zone upon sample application during a migration step. In an embodiment, the control zone is the most distal portion of the assay cassette and therefore, the sample passes into it last.

An embodiment of the invention incorporates an unique identifier 7. An unique identifier 7 in an embodiment of the invention is described as a lot number, bar code, RFQ code or other independently identifiable label. In an embodiment of the invention, the unique identifier 7 is placed upon the plastic housing.

An embodiment of the invention incorporates a labelled secondary reagent 8. A labelled secondary reagent 8 in an embodiment of the invention is described as colored latex beads or colloidal gold. In an embodiment of the invention, the extent to which an analyte becomes bound can be determined by utilization of a labelled secondary reagent 8 in association with techniques known by those skilled in the art.

In association with a method of use of an embodiment of the invention, the utilization of an application, the incorporating testing techniques associated with hCG, P4, LH, FSH and E2 as known and understood by those skilled in the art, the application operating in conjunction with a smart device, such as a smartphone or tablet, the smart device having a camera, in association with methods known by those skilled in the art, acts as the method of reading and interpreting the test cassette results. In such method of use, the user performs an applying step, where the user applies a sample to the test cassette. In embodiment, in a processing step, over a period of several minutes following the applying step, the sample processes through the test cassette into the one or more test strips 9 prior to evaluation. In an embodiment, after the processing step, the user performs an imaging step, whereby a user utilizes a camera associated with a smart phone or tablet to capture an image of the test cassette results, for further evaluation in association with an application operating in conjunction with said smart phone or tablet. During a quantifying step, the said application, configured to use calibration standards as known by those skilled in the art, will quantitate analytes involved in ovulation and early pregnancy. In the preferred embodiment in particular, will quantitate the five analytes described herein. During the computing step, the lot number or unique identifier utilized by the application operating on the smart device to determine which set of internal standards to use for comparison and evaluation of the test results, utilizing methods for comparison and evaluation of test results associated with hCG, P4, LH, FSH and E2 as known and understood by those skilled in the art. To facilitate this method, in an embodiment of the invention, the reader application can image the test cassette directly, or alternatively utilize a clip or other positioning device to hold the cassette at optimal location for imaging.

Figure 2:
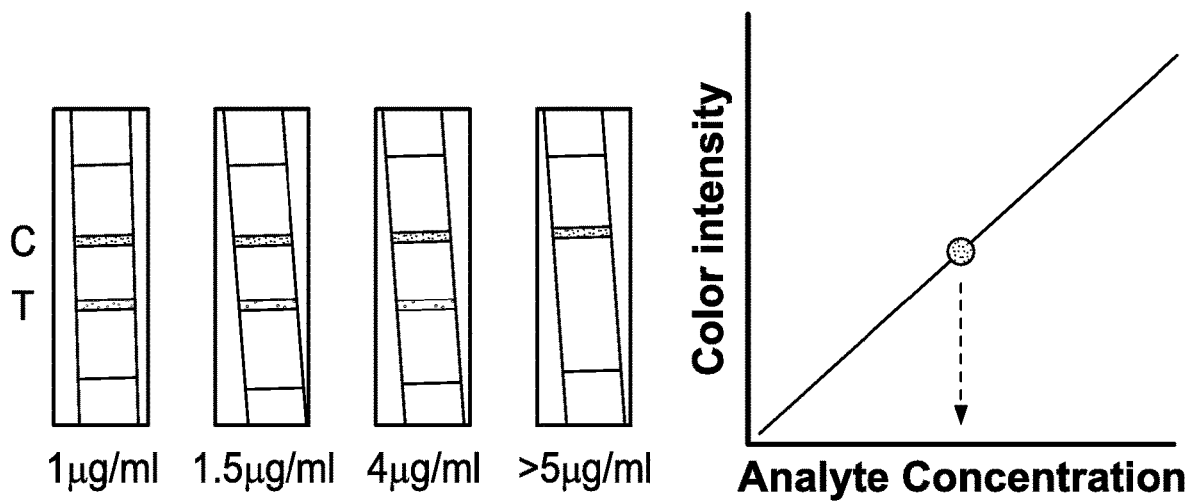
FIG. 2 depicts the color intensity of the disposable lateral flow assay test directly correlated with the concentration of the analyte in multiple samples.
Figure 3:
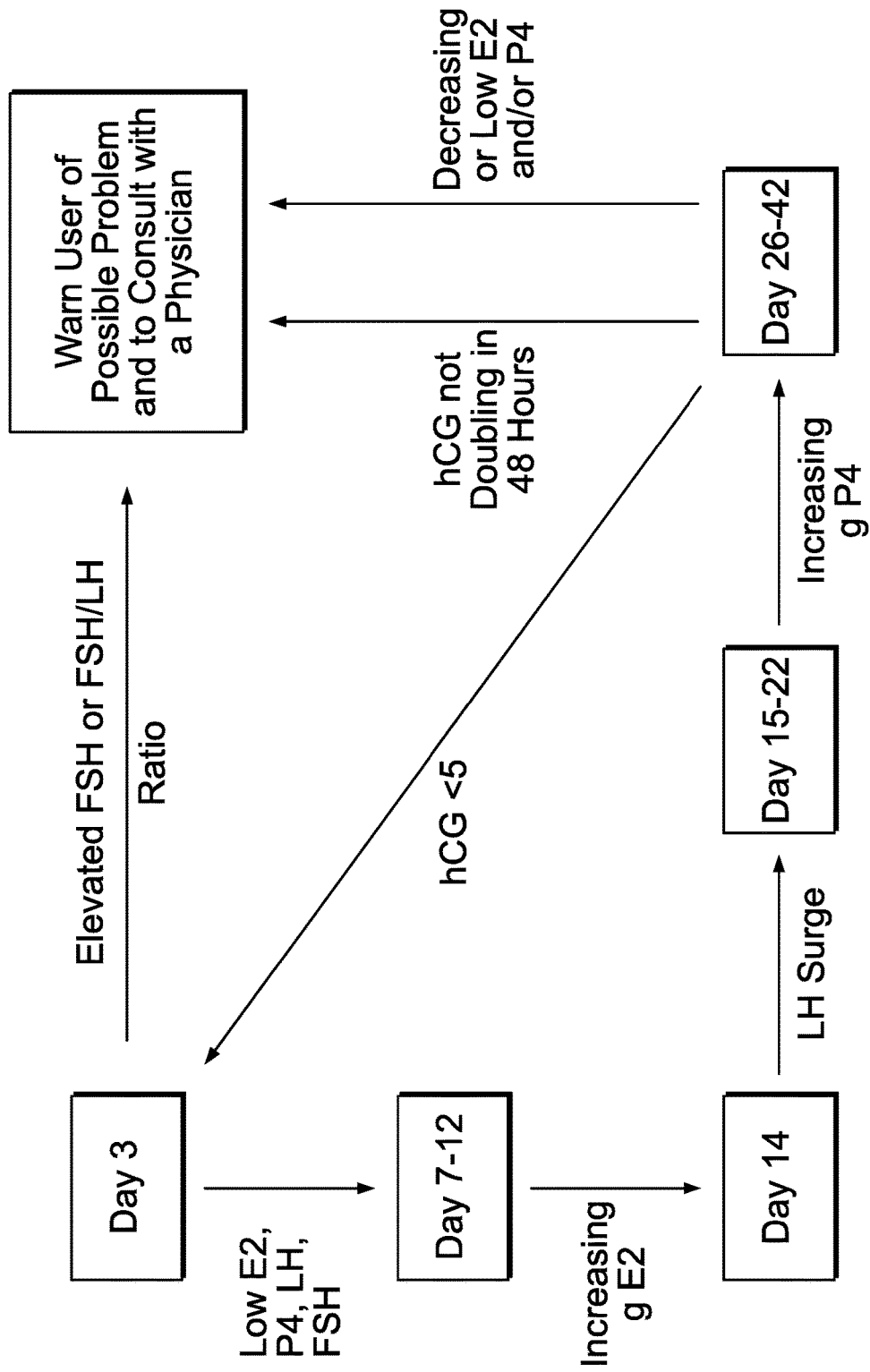
FIG. 3 depicts an exemplary flow chart of ovulation cycle monitoring using the disposable lateral flow assay of the invention.

In an alternative method of use, the Quantitation Method depicted by FIG. 2, samples of known analyte concentrations will be first applied to the test cassettes during an sampling step. During the yielding step, each concentration will yield a test line of a different color intensity. During the graphing step, the color intensities will be plotted on a graph to create a standard curve. During the assigning step, all unknown samples (pictured as a red dot in image above) that fall between the lowest and highest standard curve intensity will be assigned a concentration along the standard curve line.

The present inventors have recognized that the preferred embodiment of the invention will have several potential uses in association with ovulation cycle and early pregnancy monitoring. Such potential uses include: Diagnosing polycystic ovarian syndrome (PCOS) by calculating LH/FSH ratios on day 3 of the menstrual cycle. Abnormally high LH/FSH ratios are 2:1 or 3:1; Testing of ovarian reserve by measuring FSH levels; Measuring E2, FSH, LH, and FSH/LH ratios to diagnose menopause or perimenopause; Measuring E2, P4, LH, and FSH on day 3 of the menstrual cycle to determine ovarian activity before start of fertility medications or treatments; E2 and LH quantitation during follicular phase of ovulation cycle to determine maturation status of the growing follicle(s); E2, LH, and P2 quantitation to monitor follicular development during medicated ovarian stimulation cycles such as artificial reproductive technologies (ART), in vitro fertilization, intrauterine insemination, or timed intercourse after administering follicle-inducing medications; E2, P4, and LH quantitation to determine ovulation date; P4 quantitation in luteal phase to diagnose luteal phase defect and low or abnormal progesterone levels; hCG quantitation to diagnose pregnancy; Calculating hCG doubling times to diagnose if pregnancy is progressing normally; Monitoring E2, P4, and hCG is early pregnancy to diagnose the need for E2 and/or P4 supplementation to maintain the pregnancy; Using hormonal data from previous ovulation cycles to predict fertile and infertile times within subsequent ovulation cycles; Sharing of hormone profiles with medical professionals to facilitate improved care.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art. The terms "coupled" and "linked" as used herein is defined as connected, although not necessarily directly and not necessarily mechanically. A device or structure that is "configured" in a certain way is configured in at least that way, but may also be configured in ways that are not listed. Also, the sequence of steps in a flow diagram or elements in the claims, even when preceded by a letter does not imply or require that sequence.

I claim:

1. A diagnostic system for monitoring ovulation cycles, comprising:
   a lateral flow assay test cassette configured to simultaneously measure at least two hormones and/or analytes present within a single sample, wherein the lateral flow assay test cassette comprises:
   a sample well configured to collect and receive the single sample; and
   a test strip configured to receive the single sample from the sample well and to detect the presence of pregnanediol glucuronide (PdG) and at least one other hormone and/or analyte in the single sample, wherein the test strip comprises:
   labeled monoclonal anti-PdG antibodies of IgG isotype impregnated onto an upstream portion of the test strip, wherein the labeled monoclonal anti-PdG antibodies of IgG isotype bind to PdG present in the single sample and move with fluid flowing downstream through the test strip, wherein the monoclonal anti-PdG antibodies of IgG isotype are deposited under ATCC accession number PTA-127054;
   one or more of the following further impregnated onto the upstream portion of the test strip:
     i. labeled anti-luteinizing hormone (LH) antibodies that bind to LH present in the single sample and move with fluid flowing downstream through the test strip;
     ii. labeled anti-human chorionic gonadotropin (hCG) antibodies that bind to hCG present in the single sample and move with fluid flowing downstream through the test strip;
     iii. labeled anti-follicle stimulating hormone (FSH) antibodies that bind to FSH present in the single sample and move with fluid flowing downstream through the test strip;
     iv. labeled anti-estradiol (E2) antibodies that bind to E2 present in the single sample and move with fluid flowing downstream through the test strip;
     V. labeled anti-estrogen metabolite antibodies that bind to estrogen metabolites present in the single sample and move with fluid flowing downstream through the test strip; and/or
     vi. labeled anti-progesterone (P4) antibodies that bind to P4 that is present in the single sample and move with fluid flowing downstream through the test strip; and
   a reagent-impregnated membrane, positioned in a downstream portion of the test strip, wherein the reagent-impregnated membrane comprises a plurality of detection zones, wherein:
   PdG is immobilized by impregnation onto a first detection zone of the reagent-impregnated membrane for binding labeled monoclonal anti-PdG antibodies of IgG isotype in a competitive assay format, to indicate the presence of PdG in the single sample at a minimum concentration of 1-20 ug/mL, and
   one or more of the following are further immobilized by impregnation onto one or more additional detection zones of the reagent-impregnated membrane:
     i. anti-LH antibodies for binding LH complexed to the labeled anti-LH antibodies from the upstream portion of the test strip in a sandwich assay format, to indicate the presence of LH at a minimum concentration of 1-50 mIU/mL,
     ii. anti-hCG antibodies for binding hCG complexed to the labeled anti-hCG antibodies from the upstream portion of the test strip in a sandwich assay format, to indicate the presence of hCG at a minimum concentration of 1-10,000 mIU/ml,
     iii. anti-FSH antibodies for binding FSH complexed to the labeled anti-FSH antibodies from the upstream portion of the test strip in a sandwich assay format, to indicate the presence of FSH at a minimum concentration of 3-20 mIU/mL,
     iv. E2 for binding labeled anti-E2 antibodies in a competitive assay format, or anti-E2 antibodies for binding E2 complexed to the labeled anti-E2 antibodies from the upstream portion of the test strip in a sandwich assay format, to indicate the presence of E2 in the single sample at a minimum concentration of 25-250 pg/mL,
     v. estrogen metabolite for binding labeled anti-estrogen metabolite antibodies in a competitive assay format, or anti-estrogen metabolites for binding estrogen metabolites complexed to the labeled anti-estrogen metabolites from the upstream portion of the test strip in a sandwich assay format, to indicate the presence of estrogen metabolites in the single sample at a minimum concentration of 1-1000 ng/ml; and/or
     vi. P4 for binding labeled anti-P4 antibodies in a competitive assay format, to indicate the presence of progesterone in the single sample at a minimum concentration of 1-60 ng/ml.

2. The system of claim 1, wherein the labeled monoclonal anti-PdG antibodies of the IgG isotype impregnated onto the upstream portion of the test strip is a monoclonal anti-PdG antibody of IgG2a isotype.

3. The system of claim 1, wherein:
   E2 is immobilized by impregnation onto a detection zone of the reagent-impregnated membrane for binding labeled anti-E2 antibodies in a competitive assay format, to indicate the presence of E2 in the single sample at a minimum concentration of 25-250 pg/mL, and/or
   estrogen metabolite is immobilized by impregnation onto a detection zone of the reagent-impregnated membrane for binding labeled anti-estrogen metabolite antibodies in a competitive assay format, to indicate the presence of estrogen metabolites in the single sample at a minimum concentration of 1-1000 ng/ml.

4. The system of claim 1, wherein the sample comprises urine.

5. The system of claim 1, wherein the sample comprises saliva.

6. The system of claim 1, wherein the sample comprises serum.

7. A method for reading and interpreting the results of the lateral flow assay test cassette in a system of claim 1, comprising:
  applying a sample to the lateral flow assay test cassette;
  processing the sample through the lateral flow assay test cassette;
  imaging the sample with a smart device;
  quantifying the hormones/or analytes present within the sample; and
  computing test results with an application operating on a smart device.

* * * * *